United States Patent
Benecke et al.

(10) Patent No.: US 6,245,085 B1
(45) Date of Patent: Jun. 12, 2001

(54) ENDOSCOPIC NIPPERS

(75) Inventors: Rainer Benecke, Hesdecke; Stefan Voelzow, Hamburg, both of (DE)

(73) Assignee: Olympus Winter & IBE GmbH, Hamburg (DE)

( * ) Notice: Subject to any disclaimer, the term of this patent is extended or adjusted under 35 U.S.C. 154(b) by 0 days.

(21) Appl. No.: 09/437,710

(22) Filed: Nov. 10, 1999

(30) Foreign Application Priority Data

Nov. 19, 1998 (DE) ............................................... 198 53 305

(51) Int. Cl.[7] ................................................... A61B 17/32
(52) U.S. Cl. ............................................ 606/174; 606/205
(58) Field of Search .................................. 606/205, 174, 606/175, 206, 207

(56) References Cited

U.S. PATENT DOCUMENTS

| 5,152,779 | 10/1992 | Sanagi | 606/205 |
| 5,352,235 | 10/1994 | Koros et al. | 606/174 |
| 5,718,714 | * 2/1998 | Livneh | 606/205 |

FOREIGN PATENT DOCUMENTS

| 89 05 099 U | 9/1989 | (DE) . |
| 693 10 037 | 1/1994 | (DE) . |
| 93 20 450 U | 10/1994 | (DE) . |
| 633 002 | 1/1995 | (EP) . |
| 688 187 | 12/1995 | (EP) . |
| 700 662 | 3/1996 | (EP) . |
| 95/02365 | 1/1995 | (WO) . |
| 96/04856 | 2/1996 | (WO) . |
| 98/34543 | 8/1998 | (WO) . |

* cited by examiner

Primary Examiner—Henry J. Recla
Assistant Examiner—Anthony S. King
(74) Attorney, Agent, or Firm—Rankin, Hill, Porter & Clark LLP

(57) ABSTRACT

Endoscopic surgery nippers have a proximal end body to which is detachably affixed the proximal end zone of a tube forming the nippers' shank, the end zone being detachably fixed in the axial position while rotatable about the axis of the end body. A grip is fixed in place on the end body and another grip is pivotally supported on the first grip and has a swivel socket along the tube axis on the proximal side of the end body. A nipper head supports nipper arms and is detachably connected in rotatably and in axially geometrically interlocking manner with the distal tube end. A rod driving the nipper arms and affixed in axially displaceable and non-rotatable manner to the nipper head extends through the tube and is detachably supported at its distal end in the swivel socket. An axially free-running rotational coupling means between rod and tube includes a coupling enclosing the rod by an axially displaceable rotational interlock, the coupling being rotatable about the tube axis and being supported in axially fixed manner at the proximal side of the tube on the end body. This coupling during the assembly phase of the tube rests against the end body while rotationally interlocking with the proximal end zone of the tube.

9 Claims, 2 Drawing Sheets

ENDOSCOPIC NIPPERS

FIELD OF THE INVENTION

The invention relates to nippers having a proximal end body to which the proximal end zone of a tube constituting the nippers shank is detachably fixed in an axially stationary manner while being rotatable about its axis, and a grip solidly joined to the end body and a second grip supported on said first grip and fitted with a swivel seat along the axis of the tube and, at the proximal side of the end piece, a nipper head supporting nipper arms and rotatably, detachably connected in axially geometrically interlocking manner to the distal end of the tube and a rod which is axially displaceably, but non-rotatably, mounted to the nipper head, driving the nipper arms and passing through the tube and being detachably supported at its distal end in the swivel seat and with an axially freely running rotary coupling means between the rod and the tube.

BACKGROUND OF THE INVENTION

Such nippers are used in endoscopic surgery, in particular in laparoscopy. The nippers shank formed by the tube is of substantial length, for instance 40 cm. Its outside diameter illustratively must be 4 mm in order to be insertable through corresponding endoscopic inlets into the patient. The rod used to drive the nippers must be of high mechanical strength in order to transmit high forces, including the tube which must be of a suitable wall thickness, ensuring that there can only be space inside the tube for the rod.

The nippers head bearing the nipper arms and the tube of such nippers should be freely rotatable relative to the grip, which typically is scissors-like, in order to allow seizure at arbitrary angular positions.

When the nipper arms are appropriately shaped, the nippers also may act as scissors.

The most significant feature of the nippers of this general type is disassembly into three parts. Following appropriate unlocking, the nippers head together with the rod, the tube together with is proximal fasteners and the terminal body with the grips, can then be taken apart. This feature is required for cleaning and sterilization.

The nippers comprise a nippers head which can be geometrically and axially interlocked at the distal shank end with a screw means or in particular with a bayonet lock. However, the rotational locking of the nippers head relative to the shank is problematical because of the torques acting on the nippers.

In German patent document C1 1 970 73 73, which shows a structure outside the species, this problem is solved by a spring-loaded bayonet lock which, however, involves substantial cleaning problems because of the exceedingly constricted conditions in the shank cross-section.

In European patent document B1 0,688,187 of the species, a bayonet lock of a more advantageous design but not secured against rotation is used. Non-rotatability of the nippers head is implemented at the distal tube end by resilient clamping elements which are inside this tube and which geometrically interlock with the rod when the tube is made to abut the end body.

A similar design is provided by the European patent document A1 0,633,002 wherein a leaf spring at the shank tube may be made to geometrically interlock with grooves in the rod and be secured in place in the operative position by means of the apposed end body.

These known designs of the species implement the axial displaceable non-rotatable interlock directly between tube and rod and consequently require complex designs of rod or tube. Problems in manufacture and cleaning therefore ensue.

SUMMARY OF THE INVENTION

An object of the present invention is to provide nippers of this general type offering full operability as with those of the prior art while being simpler and more easily cleaned as regards the parts which can be dismantled from the end body.

The invention comprises a coupling rotatably supported on the end body and enclosing the rod in longitudinally displaceable but rotationally interlocking manner and in turn being made to rotationally lock onto the rod at its end face when the nippers are being assembled. Accordingly, the rotational connection of rod and tube does not take place directly between these parts but by means of a coupling rotatably supported on the end body while separate from these two parts to which it transmits their rotational linkage. As a result, the shank and the rod can be manufactured to be substantially simpler than in the state of the art, in particular being without resiliently supported elements. The shank and rod need merely be fitted with simple protrusions implementing geometric interlocking. The coupling per se may be designed substantially without regard to the constricted cross-sectional configuration in the shank zone and, remaining at the end body during disassembly, it is subjected to lesser sterility requirements. On the whole, this design is simpler, more economical and more easily cleaned.

The coupling may be permanently supported on the end body, or it may be detachable by compressing resilient stops and be moved through the end body's borehole, for instance for cleaning purposes, repairs or replacements.

When the nippers are being assembled, the tube and the rod must both be made to essentially simultaneously rotationally interlock with the coupling. Short of special design features, they would have to be moved toward the coupling both in precisely determined angular positions to allow geometric interlocking. Features are provided to bypass the work entailing such a handling procedure. Both interlocking zones of the coupling are fitted at their distal ends with trap zones to catch the mating interlocking parts of nippers and tube in the event of angular deviations and moving them in alignment for the next interlocking zone. Nippers assembly is facilitated in this manner.

BRIEF DESCRIPTION OF THE DRAWINGS

The invention is illustratively and schematically shown in the accompanying drawings wherein.

DETAILED DESCRIPTION OF A PREFERRED EMBODIMENT

Figure 1:
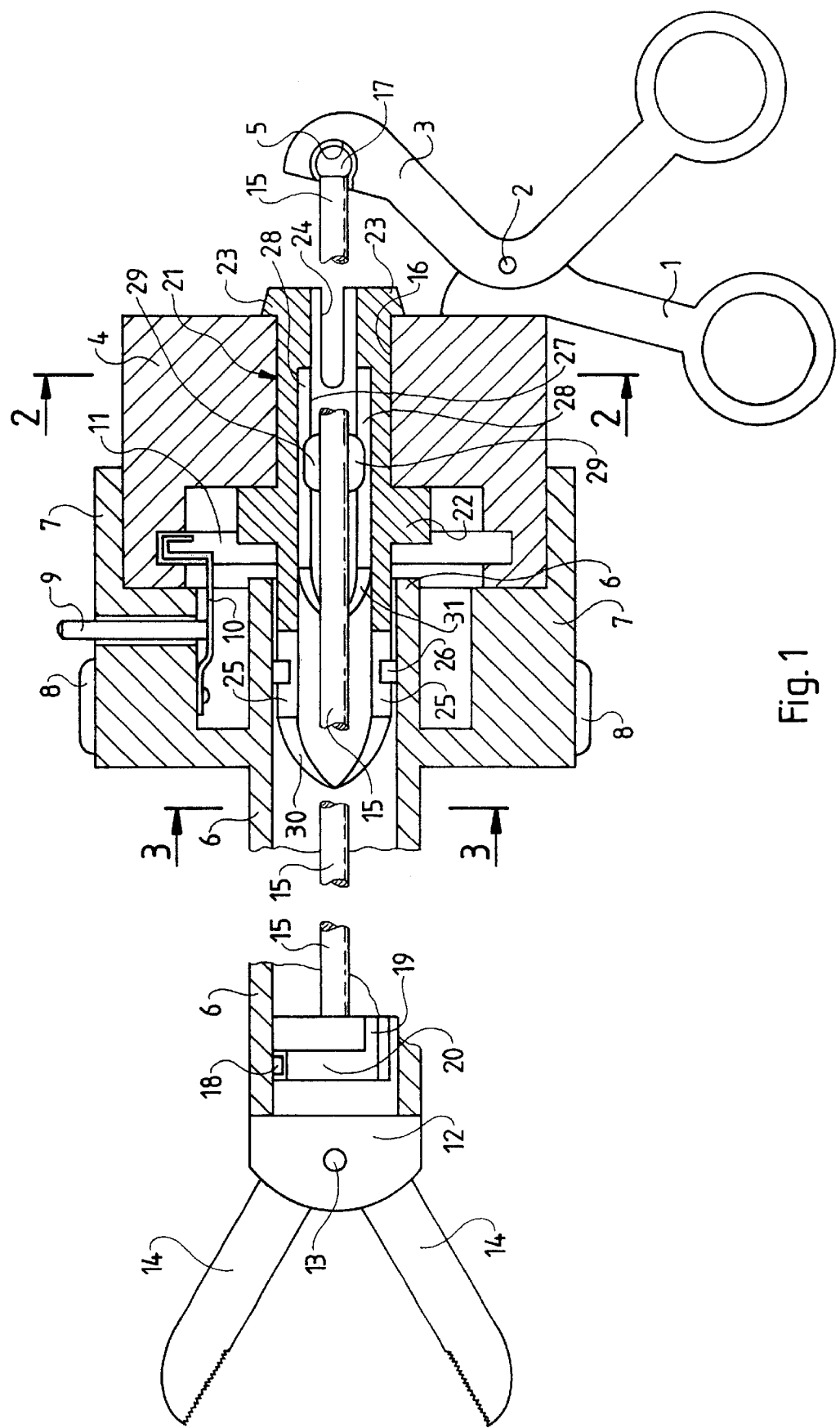
FIG. 1 is a longitudinal axial section of the nippers.
Figure 3:
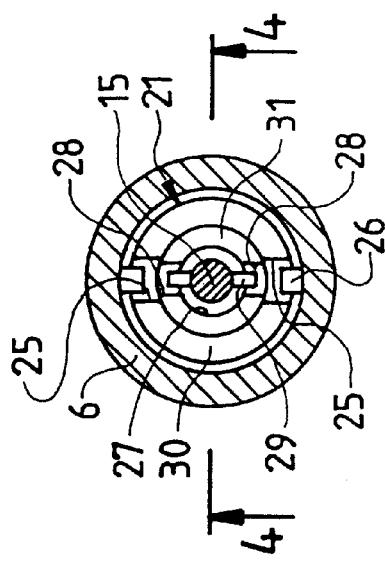
FIG. 3 is a section along line 3—3 of FIG. 1 of the rod, tube and coupling.

As shown in FIG. 1, the nippers comprise the conventional manual actuation means of a stationary grip 1 pivotally linked at 2 to a displaceable grip 3. Stationary grip 1 is fixedly attached to an end body 4. Displaceable grip 3 has at its free end a ball-head cavity 5 to implement a detachable, swiveling push-pull connection with the conventional ball.

A tube 6 constitutes the shank of a nipper head 12 and is rotatably supported, together with a bush 7 integrally attached to tube 6, on end body 4 by a mating cylindrical surface on bush 7 and an outer cylindrical surface of body 4. Bush 7 has external knurling 8 by which the bush can be manually rotated relative to the end body. A spring 10, actuated from the outside by a pin 9, lies inside of bush 7 and end body 4 and, when these parts are assembled, enters an annular slot 11 in end body 4 and axially locks tube 6 and body 4 together. However, the tube and bush remain rotatable on end body 4.

The shown nippers can be disassembled by releasing this lockable rotational coupling into a shank part and a grip part, which are mutually connectable in a rotatable manner.

Nipper head 12 is located at the distal end of the tube 6 and is connected in this embodiment to two nipper arms 14 by a pivot pin 13. A rod 15 is longitudinally movable to drive nipper arms 14 by means (not shown) in the nipper head, the rod being supported non-rotatably but in longitudinally displaceable manner on nipper head 12. Rod 15 traverses the entire tube, which is open proximally, and extends through a bearing borehole 16 in end body 4 and a ball 17 at the proximal end of the rod detachably engages ball-head cavity 5 of displaceable grip 3 in order to transmit through grip 3, by longitudinal displacement, the drive force to nipper arms 14.

Together with rod 15 affixed to it, nipper head 12 may be decoupled from tube 6. For that purpose, nipper head 12 is inserted by means of an insertion element of lesser diameter into the distal end of tube 6 where it may be secured, for instance in this embodiment, by a bayonet slot against an inner pin 18 affixed to tube 6. The bayonet slot in the surface of the insertion element of nippers head 12 comprises a transverse part 20 and an axially parallel longitudinal part 19 which is open toward the proximal end face of nipper head 12. In the secured rotational position of nipper head 12 relative to tube 6 shown in FIG. 1, inner pin 18 projects into transverse part 20 of the bayonet slot. To secure this engagement position of the bayonet lock—which, for compactness, lacks any rotation preventing means of its own—a rotational coupling means is required between rod 15 and tube 6.

The rotational coupling means is designed as a coupling 21 which is shown in different sections in FIGS. 1–4 and which is rotatably supported by its cylindrical outside surface in bearing borehole 16 of end body 4. On one hand, coupling 21 rotationally interlocks with tube 6 and, on the other hand, with rod 15. As shown in the drawings, while being rotatable, it is nevertheless held axially fixed inside bearing borehole 16, namely at its ends projecting beyond said borehole, by a fixed stop 22 and two resilient stops 23 which, when the end of coupling 21 fitted with a continuous longitudinal slot 24 at the proximal end zone is compressed, in turn are compressed and can be guided through bearing borehole 16. However, coupling 21 also may be designed to be assembled to bearing borehole 16 in other ways.

As shown in FIG. 1, the distal end zone of coupling 21 somewhat enters the proximal end zone of tube 6. There, coupling 21 is fitted with two mutually opposite, axially parallel outer slots 25 open at their ends and engaged by inside pins 26 attached to tube 6 to secure these slots against rotation. The rotational interlock of tube 6 and coupling 21 is implemented in this way when tube 6 is made to abut end body 4.

The coupling comprises a continuous axial borehole 27 having an inside diameter sufficient to pass rod 15 together with its ball-head 17. In this embodiment, continuous borehole 27 comprises two mutually opposite longitudinal channels 28 open toward the borehole and entered by radial protrusions 29 of rod 15 to achieve non-rotatability. Accordingly, coupling 21, which is coupled in rotationally interlocking manner with the geometrically interlocking system comprising axially parallel outer slots 25 and inside pins 26. The coupling 21 is also non-rotatably linked by the geometric interlocking system comprising two mutually opposite longitudinal channels 28 and radical protrusions 29 to rod 15, namely over the full range of longitudinal adjustment of rod 15, as permitted in the longitudinal channels 28.

Figure 4:
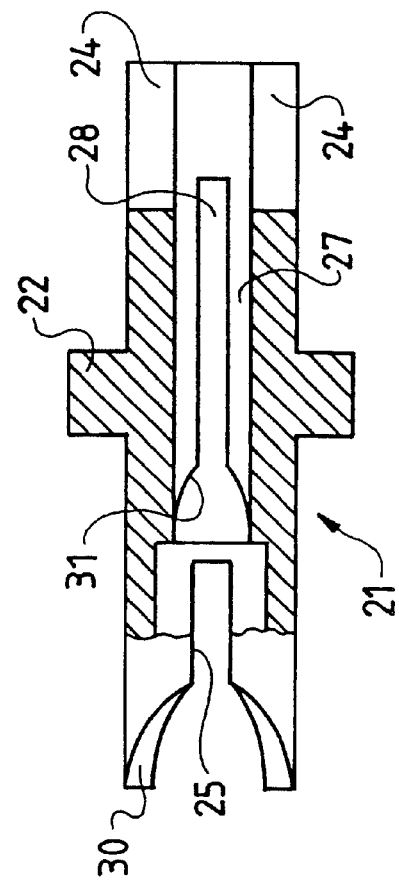
FIG. 4 is an axial section along line 4—4 of FIG. 3 of the coupling.
Figure 2:
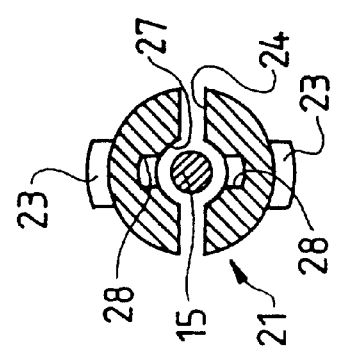
FIG. 2 is a section along line 2—2 of FIG. 1 of the coupling and the rod.

To facilitate insertion of tube 6 and rod 15 in coupling 21 to implement rotary coupling when assembling the nippers, even when the angular positions are somewhat off, trap zones 30 and 31 flaring distally are at the distal ends of both slots 25 and longitudinal channels 28, said trap zones being shown most clearly in FIGS. 1 and 4. If there is some misalignment between an inner pin 26 and a slot 25 or between a radial protrusion 29 and a longitudinal channel 28, the screw-shaped flaring walls of the trap zones 30 and 31 engage inner pin 26 or radial protrusion 29 resp. and rotate it into the proper angular position for insertion into slot 25 or longitudinal channel 28.

The above embodiment allows a number of variations in the region of coupling 21. In particular, the rotational interlock of tube 6 and rod 15 may be implemented in another manner.

In the above embodiment, the coupling 21 enters tube 6. However, this coupling also may enclose, in a manner not shown herein, this tube from the outside. The design of the engagement between pin and slot used above for rotational interlock also may be reversed with the pin being at coupling 21 and the slot being located in tube 6. Again in a manner not shown herein, coupling 21 and tube 6 may be of equal diameters and be merely fitted with end-face claws implementing rotational interlock.

The function of rotational interlock of rod 15 and coupling 21 also may be attained in another way. Illustratively, the continuous borehole 27 of the coupling 21 per se may be of non-circular cross-section to match a corresponding non-circular outside contour of the rod 15.

Even when the above mentioned variations of rotary interlock are used, matching trap zones may be fitted into the distal ends of the coupling's zones of rotational interlock to facilitate the insertion of mating parts at a somewhat misaligned angular position. Such trap zones facilitating insertion also may be present additionally or alternatively at the tube or rod.

The coupling 21 anyway being rotationally supported on the end body 4, another omitted embodiment variant allows designing tube 6 without a proximal bush 7 and to be detachably affixed directly to the coupling 21.

The shown bayonet lock comprising the inner pin 18 and the transverse part 20 between nippers head 12 and tube 6 may also be replaced by an axial connection securing said head and tube, for instance a screw connection with a short thread.

What is claimed is:

1. A nipper assembly for endoscopic surgery comprising;
   a tube (6), said tube having a proximal end, a distal end, and defining a central longitudinal axis;
   a nipper head (12) having relatively movable nipper arms (14), said nipper head being rotatably and detachably connected to said distal end of said tube (6), said nipper head (12) being axially geometrically interlocked (18, 20) to said distal end of said tube (6) so that said tube forms a shank of said nipper head;
   an end body (4), said proximal end of said tube being detachably affixed to said end body in an axially stationary manner while being rotatable about said axis, a first grip member (1) fixedly joined to said end body (4);

a second grip member (3) pivotably mounted for movement relative to said end body and said first grip member (1), said second grip member (3) having a swivel seat (5) disposed along said axis of said tube (6) and proximate said end body (4);

a rod (15) non-rotatably mounted for axial displacement relative to said nipper head (12) for driving said nipper arms (14), said rod extending through said tube (6) and having a distal end (17) that is detachably supported in said swivel seat (5); and an axially movable freely running coupling means between said rod (15) and said tube (6) to connect said rod and tube for common rotation, said coupling means including a coupling (21) through which said rod (15) extends, said rod and coupling being coupled to each other by axially displaceable interlocking means (28, 29), said coupling being supported by said end body (4) so as to be rotatable about said tube axis while being axially fixed in place relative to said proximal end of said tube (6), said coupling being interlocked (25, 26) to said proximal end of the tube (6) so as to rotate with said tube when said tube is in an assembly position.

2. The nipper assembly according to claim 1 wherein said tube comprises a pin that is received by an axial slot formed in said coupling so as to rotationally interlock said tube and said coupling.

3. The nipper assembly according to claim 2, wherein said rod includes a radially extending projection that extends through a slot formed in said coupling so as to rotationally interlock said rod and said coupling.

4. The nipper assembly according to claim 3, wherein said rod, tube, and coupling are linked for common rotation relative to said end body and about said longitudinal axis.

5. The nipper assembly according to claim 4, wherein said coupling (21) extends through a bearing borehole (16) formed through said end body (4) and projects from inner and outer ends of said borehole, said coupling (21) having a radially-projecting fixed stop (22) adjacent said inner end of said bearing borehole (16), said coupling (21) also defining longitudinal channels (24) between radially-inward compressible resilient stops (23) that engage said end body adjacent said outer end of said borehole.

6. The nipper assembly according to claim 5, wherein said coupling (21) comprises trap zones (30, 31) to facilitate assembly of said rod, coupling, and tube in the proper orientation.

7. The nipper assembly according to claim 1, wherein said coupling (21) extends through a bearing borehole (16) formed in said end body (4) and projects from inner and outer ends of said borehole, said coupling (21) having a radially-projecting fixed stop (22) adjacent said inner end of said bearing borehole (16), said coupling (21) also defining longitudinal channels (24) between radially-inward compressible resilient stops (23) that engage said end body adjacent said outer end of said borehole.

8. The nipper assembly according to claim 1, wherein said coupling (21) comprises trap zones (30, 31) to facilitate assembly of said rod, coupling, and tube in the proper orientation.

9. The nipper assembly according to claim 1, wherein said rod includes a radially extending projection that extends through a slot formed in said coupling so as to rotationally interlock said rod and said coupling.

* * * * *